United States Patent [19]

Zelman

[11] Patent Number: 4,464,337

[45] Date of Patent: Aug. 7, 1984

[54] DIALYSIS PROCESSING OF PRESERVED LIVING CELLS AND CELL COMPONENTS

[75] Inventor: Allen Zelman, Troy, N.Y.

[73] Assignee: Rensselaer Polytechnic Institute, Troy, N.Y.

[21] Appl. No.: 508,017

[22] Filed: Jun. 27, 1983

Related U.S. Application Data

[63] Continuation of Ser. No. 231,804, Feb. 5, 1981, abandoned, which is a continuation-in-part of Ser. No. 119,423, Feb. 7, 1980, Pat. No. 4,306,556.

[51] Int. Cl.³ ............... B01J 19/00; A01N 1/00; B01D 13/00
[52] U.S. Cl. ..................... 422/41; 210/647; 422/40; 435/2
[58] Field of Search ............ 422/40, 41, 44, 48; 435/2; 210/647

[56] References Cited

U.S. PATENT DOCUMENTS 3,418,209 12/1968 Ushakoff .................. 422/41 X
3,727,612 4/1973 Sayers et al. ............. 422/44 X
4,132,594 1/1979 Bank et al. ............... 422/41 X Primary Examiner—Barry S. Richman
Attorney, Agent, or Firm—McGlew and Tuttle

[57] ABSTRACT

A method and apparatus of processing biological fluids by adding or removing preservatives or simply removing water comprises providing a bag of semi-permeable membrane which contains the biological fluid and bathing the bag with dialysate having controlled osmolality. The preservative or water can thus be removed or added to the bag directly through the semi-permeable membrane by controlling the osmolality of the dialysate without exposing the biological fluid to contaminants. In the case of whole or components of blood, the blood or blood components can be collected in the bag, processed for preservation, and prepared for use then administered, all in the same bag.

8 Claims, 6 Drawing Figures

DIALYSIS PROCESSING OF PRESERVED LIVING CELLS AND CELL COMPONENTS

CROSS REFERENCE TO RELATED APPLICATION

This is a continuation of the inventor's previous application having Ser. No. 231,804 filed Feb. 5, 1981 and now abandoned which itself was a continuation-in-part of the inventor's application having Ser. No. 119,423 filed Feb. 7, 1980, now U.S. Pat. No. 4,306,556 issued Dec. 22, 1981.

FIELD AND BACKGROUND OF THE INVENTION

The present invention relates in general to cell preservation techniques and, in particular to a new and useful process and apparatus which utilizes dialysis processing to preserve living cells and cell components, particularly red blood cells.

Red blood cells, which have been frozen in the presence of glycerol, can be stored for years at −80° C. with excellent post-thaw recovery and in vivo survival.

Today, three approaches to red cell freezing and deglycerolization are in clinical use: the agglomeration method, the low glycerol method and the high glycerol procedure as modified and adopted by the American Red Cross. Estimates of the extent to which these three procedures are used in North America, based on sales of glycerol solutions during 1976 by U.S. manufacturers, total 25,000 units processed by agglomeration, 30,000 by the low glycerol method and 165,000 by the high glycerol procedure. All procedures yield a product of essentially equivalent quality. Differences in the rate of use to some extent reflect differences in processing costs as well as the very large impact of the Red Cross Blood Program which processes an estimated 50% of all units frozen in North America.

Of all the users for frozen red blood cells, probably the most important and far reaching is their use for inventory control. First, in regional blood centers, cells collected during peak collection times of the year could be maintained in storage for use in times of deficit. Second, small isolated hospitals, because of irregular needs, now must either tolerate an excessive rate of outdating or engage in an extensive exchange program with a distant regional center. Frozen red cells would be a solution for both of these inventory control problems but only provided that the glycerolization procedure was rapid, simple and economical.

Some of the problems surrounding the removal of glycerol from the high glycerol preparations have been overcome through the use of cell washing devices. One of these, developed by the Haemonetics Company (Braintree, MA) and based on the Cohn Fractionator, performs a continuous flow wash in a disposable bowl. The other apparatus developed by the IBM Corporation, conducts an automated batch wash in a disposable bag. Although effective, these devices add considerable cost to the use of frozen cells.

At the present time, the capital equipment ranges from over $5,000 to over $17,000 with the disposable plastic components ranging from about $8.00 to over $20.00. The washing protocols require a minimum of 30 minutes per unit and these devices will wash only a single unit at a time. The time required for processing of frozen red blood cells using current methods is an effective obstacle to the use of frozen red cells for emergency applications under most circumstances. On the other hand, when frozen cells are routinely deglycerolized on a large scale within a hospital, the diversion of deglycerolized cells for emergency use appears to be entirely feasible, and at least two large general hospitals have reported outdating rates of 5% and 1% or less. See Meryman, H. T., *Am. Journal of Med. Tech.* 41:265–282, 1975 and Huggins, C. E., *In: Red Cell Freezing*, AABB Workshop, PP. 31–53, 1973.

The 24 hour outdating period constitutes one of the major problems with frozen red cells today. This is particularly true when cells are deglycerolized at a blood center and delivered to a hospital at some distance. A unit of cells specifically directed to a particular patient, and then not used, frequently cannot be cross-matched for some other recipient within the 24 hour limit. The 24 hour outdating is imposed because of the hazard of bacterial contamination during processing.

Processing of multiple units imposes a special hardship where more than one unit has been deglycerolized in the Haemonetics disposable bowl. Blood centers preparing frozen red cells under Federal license are required to use a variety of safeguards to assure that all units washed through the same bowl are delivered to a single recipient. Changes in the design of the Haemonetics apparatus could obviate the need to prepare multiple units with the same bowl. Acceptable economics, however, and more rapid and simultaneous deglycerolization are a necessary goal of blood banking.

Cost continues to be the predominant disadvantage of frozen red cells, although one large general hospital reports that, since converting almost entirely to frozen or washed red cells, the cost per thousand units of matched, frozen cells is only 44% more than matched whole blood. At the present time, disposable supplies for glycerolization and deglycerolization total at least $35.00 per unit. The present scale of red cell freezing is already sufficient to obtain cost reductions from volume production and it seems unlikely that substantial further reductions in the costs of disposables can be anticipated.

Another problem which adds to the cost of frozen red blood cells (RBC) is the rate of hemolysis that is the destruction of RBC's due to rupturing of the cell membranes. Hemolysis during deglycerolization accounts for up to 12% loss of the red blood cells. The various sterile solutions used in RBC washing lowers the osmolality too fast for the cells to accommodate and the cells rupture. These losses are also obviously a major cost factor.

All methods of long term storage of glycerolized red blood cells require freezing between −10° C. and −80° C. There is a significant problem associated with maintenance of such low temperatures in special freezers. Should a power failure occur, in order to preserve the stored blood, emergency power units are required. If the freezer fails, substantial loss of stored blood may occur.

SUMMARY OF THE INVENTION

The present invention provides a method and apparatus for both glycerolization and deglycerolization, based on the use of a blood bag composed entirely of semi-permeable membrane material. Because the membrane itself would form an absolute barrier for pyrogens, viruses and bacteria, costly sterile solutions are totally avoided. Since the blood can be collected and"

maintained in a sterile environment in the same bag, the 24 hour outdating period can be greatly increased.

The process is easily automated and carried out without technician attendance. Processing of multiple units simultaneously could be accomplished without fear of cross contamination inasmuch as each blood unit is contained within its own membrane system and lastly, the cost would undoubtedly be greatly decreased because membrane material is not very expensive and no sterile solutions are needed.

Objections to using membranes, comparable to those used in hemodialysis, for such a procedure, would be that homoglobin and cell fragments formed during the freezing-thawing process could be washed out as in prior art methods. Hemolysis can, however, be eliminated by a gentle washing procedure. The only other objection to this membrane process is the reduction of white cell fragments. Administration of whole blood, however, has similar consequences. Recently a leucocyte filter (Termo Corp., Tokyo, Japan) has been introduced which may eliminate this objection, however.

According to the invention the bag made of semipermeable membrane material can also be utilized to contain body or biological fluids other than blood which must be preserved. Also, in addition to the cryopreserving technique, the invention can be utilized to chemically preserve body fluids. In the case of blood or blood components such as red blood cells, the inventive apparatus and process can be used to add glycerol or other preservatives to the medium to be stored, to regulated levels. For example, glycerol can be added to red blood cells, to a level of 2 molar glycerol for freezing at $-20°$ C., 3.5 molar glycerol for freezing at $-80°$ C. or glycerolization can be continued for dehydrating, the red blood cell suspension for storage above $0°$ C. In this latter case, the glycerolizing solution can also be deoxygenated and be used with commonly added anti-oxidants such as vitamin C, vitamin E, BHT, BHA or other chemical additives. As a result, the red blood cells are left in a dehydrated, deoxidized oxidation protected state but one which is still liquid. This process can be termed "chemical freezing" and can be effective in preserving red blood cells or other perishable cells and components without the requirement for freezing such components.

While the "chemical freezing" technique is applied to red blood cells or blood components, it should be understood that the present application is applicable in preserving all manner of living or dead cells and/or cell components and other biological specimens or fluids including but not limited to, red blood cells, white blood cells, platlets, other cell bodies, blood chemical components, bone marrow cells, plasma, cerebral spinal fluid, other body or biological fluids, transfused suspended cells, and the like. Such various specimens or fluids can also be preserved according to the other methods of this invention.

Accordingly, an object of the present invention is to provide a method of preserving a biological specimen containing water comprising, storing the specimen in a bag of semi-permeable membrane, supplying a dialysate of controlled concentration of preservative, e.g. glycerol, over the bag to draw water out of the bag through the semi-permeable membrane and to replace that water, wholly or in part with preservative, whereby the specimen is brought to the necessary concentration of preservative suitable to store the specimen under specific conditions of temperature as previously noted.

Another object of this invention is to provide such a method wherein the fluid is red blood cells, other blood components, or other cells or cell bodies, the glycerol concentration being brought to a very high level, deoxygenated and with added anti-oxidants so that the red blood cells, etc. are deoxygenated, dehydrated and stored in preservative, by the process.

Another object of the present invention is to provide a method of removing a preservative from a biological fluid contained with the preservative in a bag having a semi-permeable membrane comprising, supplying a dialysate over a surface of the bag, the dialysate having an initially relatively high osmolality to protect the cellular components from osmotic rupture while preservatives leave the bag through the semi-permeable wall at a selected rate, agitating the fluid in the bag to reduce a boundary layer adjacent the wall, and decreasing the osmolality of the dialysate supplied over the bag surface to control the flow of the osmotic protective agent out of the bag as concentration of the preservative in the bag decreases.

A further object of the invention is to provide apparatus for achieving the aforementioned methods.

Another object of the invention is to provide such methods and apparatus which increase the speed and efficiency with which preserved living cells, cell components or other biological fluids can be processed to prepare them for use.

The various features of novelty which characterize the invention are pointed out with particularlity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
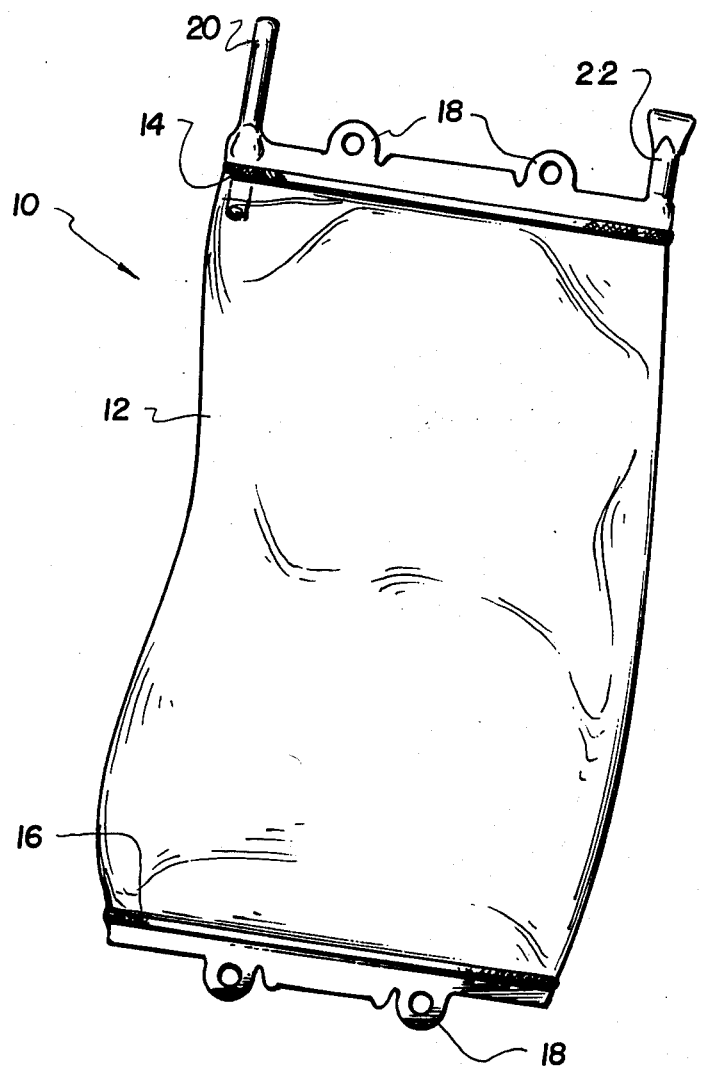
FIG. 1 is a perspective view of the inventive blood bag having a semi-permeable membrane wall.

Turning to the drawings in particular, the invention embodied therein, in FIG. 1 has as its essential component a blood bag of semi-permeable membrane generally designated 10. While the bag is termed a "blood bag", it can be utilized for any biological or chemical fluid which must be preserved then processed for use. This includes all living or dead cells or cell components, serums, other liquids, suspensions of white blood cells, marrow cells, human and non-human cells, etc.

Bag 10 can be formed from a sleeve of semi-permeable membrane 12 which is heat sealed at the top 14 and bottom 16. The bag may include one or more plys of the material and/or an additional reinforcing matrix for strength. The material extending beyond sealing areas 14 and 16 include eyelets 18 to facilitate hanging of the bag and inlet or exit ports 20 and 22.

Figure 2:
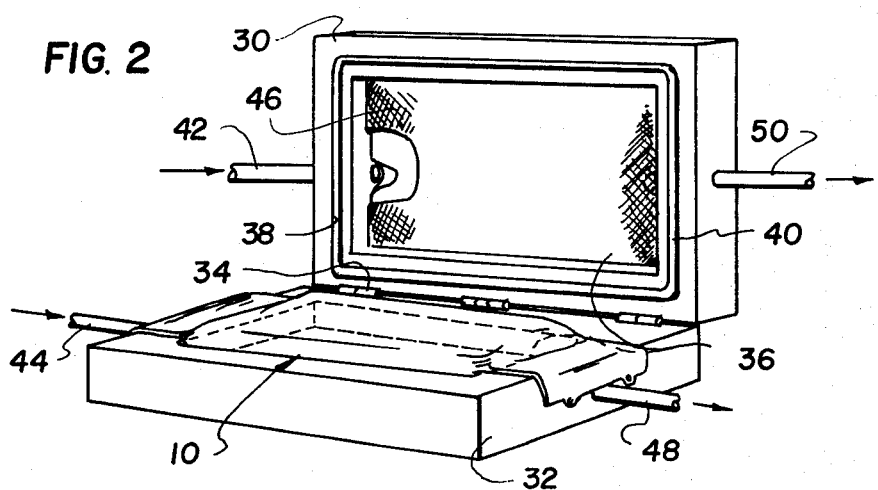
FIG. 2 is a perspective view with portions cut away for clarity of a cell for receiving the blood bag of FIG. 1 according to the invention.

A transport cell for receiving the blood bag for treatment is shown in FIG. 2. The cell comprises a top half 30 and a bottom half 32 which are connected together for example, by hinges 34. Spaces are machined into to top and bottom cell halves 30, 32 to form a chamber 36 which receives the blood bag 10. An annular canal 38 can be machined into either or both of the cell halves. An O-ring 40 is positioned in the one or more annular canals 38 and bears against portions of the blood bag squeezed between facing surfaces of the top and bottom cell halves, when the transport cell is closed on the bag.

A dialysate prepared according to the invention is supplied through inlet openings 42 and 44 into the space of chamber 36 not occupied by the bag itself. The dialysate passes a plastic or other mesh layer 46 which acts both as a dialysate mixer to mix the components of the dialysate and as a membrane supply means for distributing the dialysate over the surface of the blood bag. The blood bag substantially fills the chamber 36 so that the walls of semi-permeable membrane 12 are supported securely against the chamber walls including the mesh structures 46. The dialysate is removed from either side of bag 10 through outlet openings 48 and 50.

According to one embodiment of the invention the dialysate which is first supplied to the top half of chamber 36 over bag 10 is then channeled out of outlet opening 50 and into inlet opening 44 where it is circulated against the lower surface of bag 10. In another embodiment of the invention which treats the blood bag more rapidly, dialysate is supplied in parallel to both the inlet openings 42 and 44 and then simultaneously removed from outlet openings 48 and 50 and discharged to a drain.

For convenience of use, the transport cell can be designed as a "waffle iron" like structure which permits the easy exchange of blood bags. The transport cell may be designed to enclose one or more bags simultaneously. The bag is also of a volume to substantially fill the chamber 36, in addition to support of the walls, for the prevention of osmosis due to plasma proteins from swelling the bag and diluting the red blood cells therein.

A preferred semi-permeable material is polycarbonate membrane which is available from American Membrane of Covina, Calif.

In experiments that have been run with the apparatus of this invention, bags have been constructed and filled with 350 ml of outdated human blood which has been glycerolized according to the standard procedures set by the American Red Cross. Bags having an area of about 1920 square centimeters and about 2,800 square centimeters have been used. The transport cell used was approximately one foot by two feet in dimension.

Figure 6:
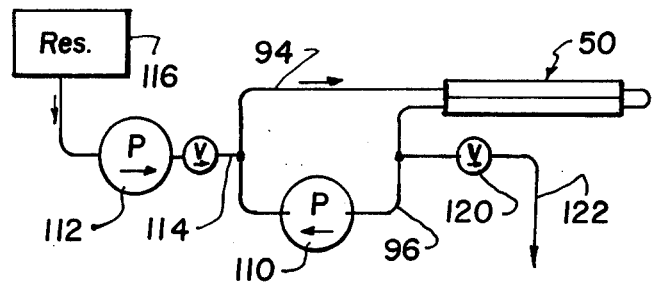
FIG. 6 is a view of another embodiment of the invention.

In addition, glycerolization has been accomplished with the device itself in the following way. Referring to FIG. 6, the transport cell 50 is disconnected from the dialysate delivery system 82 and the inlet line 94 is connected to the outlet line 96. A circulating pump 110 is connected between the inlet and outlet lines to circulate dialysate, around the circuit. Glycerol with appropriate electrolytes are added to the circulating lines 94, 96 by another pump 112 over a line 114. Pump 112 draws glycerol from a reservoir 116. In this way the glycerol concentration gradually increases and glycerol enters the blood bag. Glycerol is continuously fed to the dialysate until its concentration reaches about 3.5 molar at which time the amount of glycerol added exactly duplicates the method prescribed by the American National Red Cross for freezing preservation at −80° C. This level can be achieved in a period of about two hours. To conserve the amount of volume in the closed circuit a one way valve 120 is provided which connects to the lines 94, 95 and drains into a waste receptacle 122 or the like. Valve 120 may be a so called duck bill valve which opens only when fluid is added over line 114.

Figure 3:
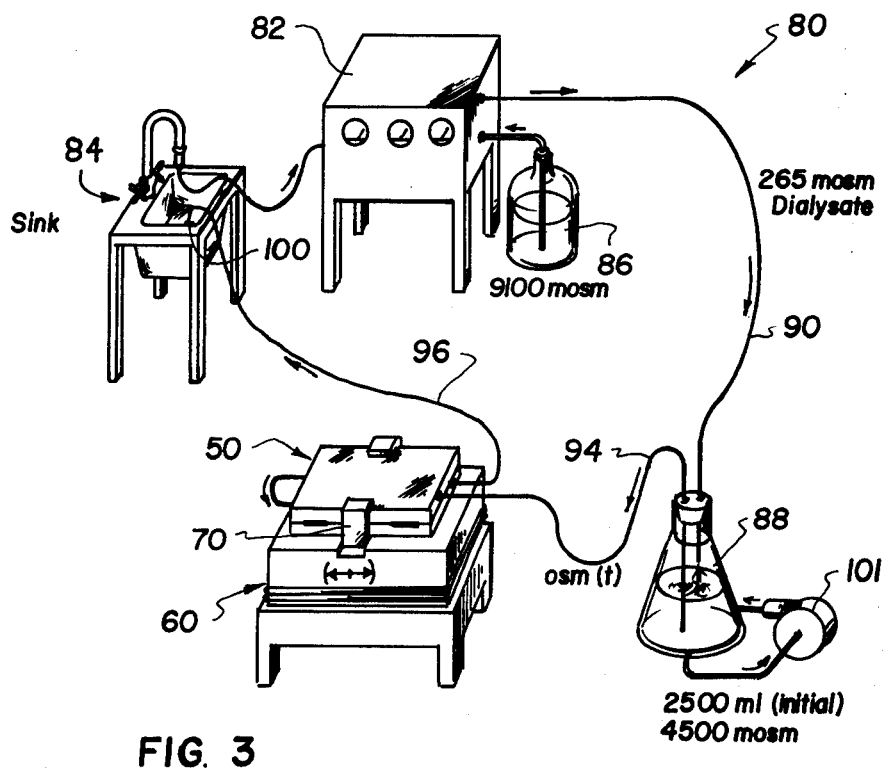
FIG. 3 is a perspective simplified view of a system according to the invention.

An important feature of the invention which is illustrated in FIG. 3 is that the fluid in the bag be agitated to prevent the buildup of a boundary layer of water which slows the addition or removal of preservative, specifically glycerol, to or from the blood bag. Agitation may be provided by known shaker devices which shake the entire cell at 10 to 600 cycles per minute. Agitation can also be provided by vibrators for vibrating a cell, rocking devices which rock the cell back and forth, soundwaves, heat or physical kneading contact on the bag surface or pulsified flow of the dialysate. When the bag is being processed to remove preservative therefrom, it has been found that glycerol moves out of the bag substantially slower than the rate at which water enters the bag. As a consequence, a boundary layer is produced between the bag and the blood which is very low in glycerol concentration. This impedes glycerol removal while, at the same time water continues to enter the bag due to the extremely high osmotic pressure of glycerolized blood which is typically on the order of 4,500 mosms. According to another feature of the invention which will be treated in greater detail hereinunder, the osmolality of the dialysate is reduced with time in a programmed fashion to control the removal of the osmotic protective agent from the bag. With such decrease, and since glycerol will no longer be able to leave the bag through the internal boundary layer, the osmotic pressure difference between the blood and the dialysate increases with time forcing more and more water into the bag. In an extreme case, the bag can burst. Agitation of the bag has been found to alleviate this condition by dispersing the materials and preventing the formation of the boundary layer adjacent the bag wall within the bag interior.

Turning to FIG. 3 which shows one overall system for practicing the invention, a transport cell generally designated 50 containing a blood bag is mounted on an agitation device generally designated 160 which may be, for example, a shaker, vibrator, rocker or the like. Cell 50 is connected to table 60 by clamps 70 and hooked up to supply and discharge lines of a dialysate supply circuit generally designated 80. The circuit 80 includes means for controlling the osmolality of the dialysate supplied to the cell 50. If glycerol is removed too rapidly from the blood bag 10, this can lead to osmotic hemolysis or rupturing of the red blood cells due to an excessive imbalance in the conditions between the interior of the red blood cells and the surrounding fluid in the blood bag. Such hemolysis of course is to be avoided. Osmolality can be controlled using an osmotic protective agent that may be the preservative itself or a additive such as salt water.

Tap water is drawn from a sink 84 by a dialysate delivery system 82 (B-D Drake-Willock, Portland, OR) commonly used for hemodialysis. This system produces dialysate at rates of up to 600 ml/min at 38° C. by diluting a concentrate from a tank 86 with tap water. The freshly made dialysate is piped over line 90 to a mixing flask 88 containing about 2500 ml of dialysate at osmolality between 4 and 7 osmole. As the dialysate is forced into the flask the dialysate leaving the flask and entering the transport cell over line 94, varies in osmolality with time according to Table I.

TABLE I
Exponential Decay of Dialysate Osmolality $$C_D(t) = C_D(o) + (C_{Conc} - C_D(o)) \mathrm{Exp}\left(\frac{Q_D T}{V_{Tank}}\right)$$

$C_D(o) \to C_{Tank}(t) \to C_D(t)$

| Dialysate Delivery System (82) | Concentrate Tank (86) | Dialysate to Transport Cell (94) |
|---|---|---|

Where: T is time; $Q_D$ is the constant rate of volume flow to the transport cell; $V_{Tank}$ is the volume of the concentrate tank; $C_D(o)$ and $C_{Conc}(o)$ are the incoming dialysate and initial tank concentrate concentrations respectively and are constant in time.

This method of dialysate delivery produces a very smooth exponential decay from very high osmolality to that of chosen dialysate. The salt concentrations of the blood bag after deglycerolization will be essentially that of the dialysate and are listed in Table II for this experiment. Other concentrations can be easily substituted for those chosen here. It is noted that while the osmolality must be carefully controlled when preservative is removed so that the removal is as fast as possible; when preservative is to be added, to preserve blood or other fluid, cells or cell parts, since this can be done more slowly, the control need not be as exact. An osmotic protective agent such as salt water is thus more useful during the removal cycle to speed removal so that the blood or other substance can be made ready for the recipient.

TABLE II
Composition of Dialysate at 265 mosm

| | |
|---|---|
| $Na^+$ 130 meq/L | $Cl^-$ 102 meq/L |
| $K^+$ 2 meq/L | $Ac^-$ 31 meq/L |
| $Mg^{+2}$ 1 meq/L | Glucose 200 mg % (11.1 m M) |

Having passed through the transport cell 50, the glycerol dissolved in the dialysate is transported over line 96 to the sink drain 100. The circulation pump on the flask maintains a well mixed solution.

Three variables for optimization of the process are: (1) The initial dialysate osmolality need to prevent hemolysis (2) The fastest rate at which the osmolality may be lowered without hemolysis and (3) How long should dialysis continue before the glycerol is at acceptable levels (<200 mosm).

Since it is known that initiating dialysis with an osmolality above that of the initial glycerol would prevent hemolysis, a research program was initiated to determine an optimum value of $$\left(\frac{Q_D T}{V_{Tank}}\right)$$

as given in Table I.

After each experiment the extracellular fluid was checked for plasma hemoglobin. In 29 of the experiments, 11 showed zero hemolysis with an average change in plasma hemoglobin of 183 mg % ±203 mg % with a range of $0 +_o 500$ mg %. The American Red Cross sets the limit of plasma hemoglobin for reinfusion at 500 mg %. Thus even with the outdated blood, which was used and which is very fragile, the method excels in preventing red cell losses.

Figure 5:
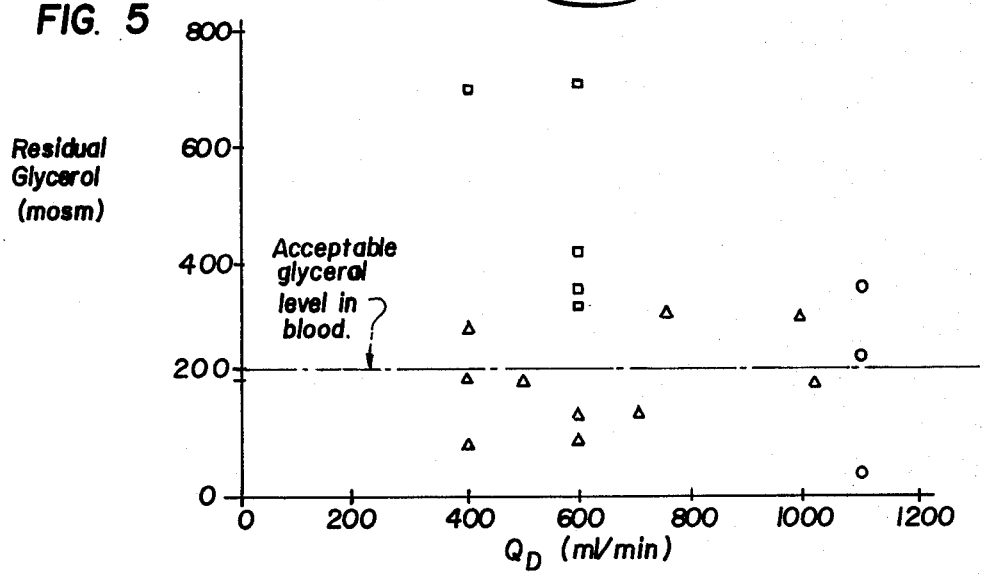
FIG. 5 is a graph showing some experimental results.

It has been found that a satisfactory initial value for the osmolality is about 4,500 mosm which can be increased to 7,000 mosm. FIG. 5 shows a table of data produced by a few initial experiments indicating the residual glycerol in the blood bag plotted against the flow of dialysate. The points indicated by a square show results after one half hour at the indicated flow, the points indicated by triangles show the results after 45 minutes, and the points indicated by circles show the results after 60 minutes. The osmolality of the dialysate was provided by sodium chloride. An acceptable flow rate has been found to be between about 200 and 2,000 ml/min. These flows have been found to be capable of reducing the glycerol content of the blood within the inventive blood bag to acceptable limits within about one half hour.

The apparatus was adjusted slightly to add glycerol to the red blood cells in the following way: the transport cell was connected to a circulating loop consisting of a pump for adding chemical preservative (glycerol), a pump for circulating the fluid around the loop and a duck bill one way valve that allowed fluid to exit the circuit while the preservative pump force preservative into the circulating loop. In this way the preservative could be increased exponentially to the red blood cells in the bag without hemolysis and the volume in the circulating loop remain constant. To prevent hemolysis the glycerol osmolality was exponentially increased to 3,500 mosm, and the electrolyte osmolality remain constant during two hours of dialysis. This time can be adjusted according to the shaking rate (160 rpm in the experiment), the volume of cells in the bag, the temperature and the osmolality of salts in the fluid surrounding the cells which in turn can be regulated by the concentration of salts in the dialysate circulating around the bag. As the glycerol concentration exceeds 4,000 mosm, the cells begin to lose oxygen; thus glycerolizing with deoxygenated glycerol can remove both water and oxygen from the cells. Without oxygen or water, most metabolic processes will slow to a great extent and the cells can be stored in a refrigerator. This forms the basis for what is herein termed "chemical freezing".

The apparatus of FIG. 3 includes a circulating pump 101 which circulates the contents of flask 88. Flask 88 as it is supplied by the dialysate at initial value from dialysate delivery system 82 produces an exponentially decreasing osmolality in the dialysate supplied through line 94 to the transport cell 50. The flask with circulating pump thus comprises osmolality varying means. These means can be replaced by any other suitable arrangement for providing an increase or decrease in osmolality depending on whether the preservative in the fluid of the blood bag in transport cell 50 is to be removed or added. For example, the osmolality must be changed from about 4,000 mosm to 265 mosm over a selected one half hour period to smoothly reduce the concentration of glycerol in a glycerolized unit of blood within blood bag 10 so as to prepare it for use, or the osmolality may be increased from 290 to 4,000 mosm by adding glycerol and appropriate additive (such as NaCl) over an hour period for preparing the cells for storage.

Figure 4:
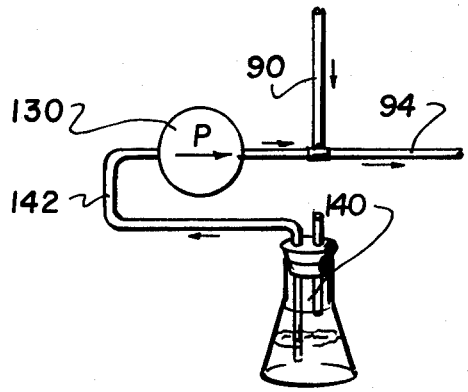
FIG. 4 is another embodiment of the inventive system shown in simplified perspective.

Turning to FIG. 4, an alternate embodiment of the osmolality varying means is shown. In FIG. 4, the dialysate from dialysate delivery system 82 is provided by line 90. The dialysate from the delivery system 82 is "isotonic medium" that is, it has the same osmolality as the substance within the bag 10. This base osmolality is modified by a feedback control pump 130 which modifies the osmolality of dialysate supplied through line 94 to the transport cell 50. As with FIG. 3 in the embodiment of the invention wherein the preservative such as glycerol is removed from a blood bag, the osmolality is initially supplied at relatively high value (for example, 6,000 mosm) and gradually for example, exponentially, reduced to the isotonic level. Such a feedback controlled pump has been manufactured and tested for use in this system using a B-D Drake-Willock blood pump as the base.

In FIG. 4, a reservoir of preservative 140 is connected over line 142 to the input of metering pump 130 which, in a metered fashion, supplies the preservative into the lines 90, 94 which are here connected to each other and bypass the provided structures in FIG. 3.

It is noted that the dialysate delivery system 82 which was used is the model N40145D B-D Drake-Willock Hemodialysis System, Portland, OR 97222.

This and the other apparatus of the invention can be utilized both for gradually feeding preservative into the bag and also for gradually removing preservative from the bag as required. While according to the preferred embodiments of the invention the specimens to be preserved are stored in the bags, it is understood the bags can be used only for the purpose of adding or removing preservative and that the specimens with or without preservative can be stored other than in the bags themselves.

While specific embodiments of the invention have been shown and described in detail to illustrate the application of the principles of the invention, it will be understood that the invention may be embodied otherwise without departing from such principles.

What is claimed is:

1. A method of preserving a specimen of blood or blood components containing water and living cells comprising:
    providing a sealed bag, for containing one unit of the specimen, made of semi-permeable membrane which is permeable to a preservative and has at least one port for entry of the specimen
    collecting the specimen in the sealed bag of semi-permeable membrane through the port;
    sealing the port so that the bag can be handled and stored as a portable unit of the specimen;
    supplying a dialysate, including glycerine as the preservative, over the bag to draw water out of the bag through the permeable membrane, whereby the specimen is dehydrated and preserved by glycerolization;
    the preservative containing highly dehydrated, deoxygenated glycerol with anti-oxidant whereby the cells are dehydrated, deoxygenated and ready for storage in the bag; and
    storing the bag with the contained specimen and preservative as a unit of the specimen.

2. A method according to claim 1, wherein the sealed bag comprises a sleeve of semi-permeable membrane heat-sealed at spaced locations to form a volume therebetween for containing the specimen.

3. A method of adding a preservative of a biological specimen comprising:
    providing a sealed bag having a semi-permeable wall which is permeable to the preservative and has at least one port for entry of the specimen;
    supplying the specimen to the bag through the port;
    sealing the port so that the bag with the contained specimen is transportable for storage and handling as a unit of the specimen;
    positioning the bag with its contained specimen in a transport cell;
    supplying a dialysate which includes the preservative, over an outer surface of the bag wall in the cell, the dialysate having an initial osmoality similar to the osmolality of the contents of the bag to cause preservative to enter the bag through the semi-permeable wall;
    agitating the specimen in the bag to reduce a boundary layer adjacent its wall;
    increasing the osmoality of the dialysate supplied over the bag surface to control the flow of preservative in the bag as the concentration of preservative in the bag increases;
    removing the bag from the transport cell with its contained specimen to which preservative has been added; and
    storing the bag as a unit of the specimen.

4. A method according to claim 3, wherein the specimen comprises packed cells, the sealed bag being made of a sleeve of semi-permeable material heat-sealed at spaced locations to form a volume therebetween for containing the specimen.

5. A method according to claim 3, wherein the sealed bag comprises a sleeve of semi-permeable material heat-sealed at spaced locations to form a volume therebetween for containing the specimen.

6. A method according to claim 3, including again positioning the bag with its contained specimen to which preservative has been added within a transport cell, after the bag has been stored as a unit of the specimen;
    supplying a second dialysate over a surface of the bag, the second dialysate having an initial relatively high osmoality of the preservative which has been added to the bag;
    again agitating the specimen in the bag to reduce a boundary layer adjacent the wall; and
    decreasing the osmoality of the second dialysate supplied over the bag surface to control the flow of preservative out of the bag as the concentration of the preservative in the bag decreases.

7. A method according to claim 3, wherein the step of supplying the specimen to the bag comprises a step of initially collecting the specimen from a natural source.

8. A method according to claim 7, wherein the specimen comprises whole blood.

* * * * *

UNITED STATES PATENT OFFICE
CERTIFICATE OF CORRECTION

Patent No. 4,464,337      Dated August 7, 1984

Inventor(s) Allen Zelman

It is certified that error appears in the above-identified patent and that said Letters Patent are hereby corrected as shown below:

In Column 1, between lines 3 and 4, add the following:

--STATEMENT OF GOVERNMENT INTEREST

The Government has rights in this invention pursuant to grant number HL-24466 awarded by the Department of Health and Human Services.--

Signed and Sealed this

Thirtieth Day of December, 1986

*Attest:*

DONALD J. QUIGG

*Attesting Officer*      *Commissioner of Patents and Trademarks*